(12) United States Patent
Maloisel

(10) Patent No.: US 8,138,306 B2
(45) Date of Patent: *Mar. 20, 2012

(54) SEPARATION METHOD

(75) Inventor: Jean-Luc Maloisel, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 756 days.

This patent is subject to a terminal disclaimer.

(21) Appl. No.: 10/499,883

(22) PCT Filed: Dec. 17, 2002

(86) PCT No.: PCT/SE02/02350

§ 371 (c)(1),
(2), (4) Date: Jun. 21, 2004

(87) PCT Pub. No.: WO03/051484

PCT Pub. Date: Jun. 26, 2003

(65) Prior Publication Data

US 2005/0043522 A1 Feb. 24, 2005

(30) Foreign Application Priority Data

Dec. 19, 2001 (SE) .................................. 0104353

(51) Int. Cl.
*A61K 38/00* (2006.01)
*C07K 1/00* (2006.01)

(52) U.S. Cl. ........................................................ 530/344

(58) Field of Classification Search ................ None
See application file for complete search history.

(56) References Cited

U.S. PATENT DOCUMENTS 5,086,167 A 2/1992 Awad, Jr.

FOREIGN PATENT DOCUMENTS

| AU | 20062940 | | 1/2001 |
|----|----------|---|--------|
| FR | 2796071  | * | 1/2001 |

OTHER PUBLICATIONS

Oscarsson et al. Amphiphilic agarose-based adsorbents for chromatography. Comparative study of adsorption capacities and desorption efficiencies. J Chromatogr. A. 1995. vol. 689, pp. 3-12.*
Ma et al. The Cation-Pi Interaction. Chem. Rev. 1997. vol. 97, pp. 1303-1324.*
Oscarsson et al. Salt-promoted adsorption of proteins onto amphiphilic agarose-based adsorbents. J Chromatogr. A, 1998, vol. 803, pp. 83-93.*
What is the pI of IgG. Accessed online at http://www.bio.net/bionet/mm/immuno/1998-February/011801.html on Dec. 18, 2006.*
Hhoribata et al. Purification, Characterization, and cDNA Cloning of a Novel Acidic Endoglycoceramidase from the Jellyfish, Cyanea nozakii. J Biol. Chem. 2000. vol. 275, No. 40, p. 31297-31304.*
Translation of FR2796071. Claims (2 pages) and description (9 pages).*
G-CSF protein, Genway. http://www.genwaybio.com/product_info.php?products_id=220020, Accessed online Mar. 25, 2009. 3 pages.*
Amersham Biosciences. Phenyl Sepharose 6 Fast Flow (low sub) and Phenyl Sepharose 6 Fast Flow (high sub). Instructions. 1997. pp. 1-4.*
Andersson, Mikael, et al., "The influence of the degree of cross-linking, type of ligand and support on the chemical stability of chromatography media intended for protein purification" Process Biochemistry, vol. 33, No. 1, 1998 pp. 47-55.
Lim, S., et al., "Purification of monoclonal antibodies from ascitic fluid using preparative electrophoresis" Journal of Chromatography A, 827 (1998) 329-335.

* cited by examiner

*Primary Examiner* — Marcela M Cordero Garcia

(57) ABSTRACT

The present invention relates to a method of separating a compound from a liquid, which method comprises providing a separation matrix comprising at least one uncharged ligand; providing a liquid wherein the compound to be separated is present in a positively charged state; contacting said matrix with said liquid to adsorb the compound; and removing the liquid. The uncharged ligands possess a quadrupole or dipole moment, allowing for a cation-π interaction between the compound and the ligand. The present invention also encompasses the use of a separation matrix, which comprises an uncharged group that possesses a quadrupole or dipole moment, in said method.

5 Claims, 6 Drawing Sheets

SEPARATION METHOD

This application is a filing under 35 U.S.C. § 371 and claims priority to international patent application number PCT/SE02/02350 filed Dec. 17, 2002, published on Jun. 26, 2003 as WO 03/051484 and also claims priority to patent application number 0104353-8 filed in Sweden on Dec. 19, 2001; the disclosures of which are incorporated herein by reference in their entireties.

TECHNICAL FIELD

The present invention relates to the field of separation, and more specifically to a method of separating a compound from a liquid, which method is based on a novel principle of adsorbing a desired compound to a chromatographic matrix. The invention also encompasses a matrix useful in such a method.

BACKGROUND

One of the most widely used separation methods is chromatography. The term chromatography embraces a family of closely related separation methods. The feature distinguishing chromatography from most other physical and chemical methods of separation is that two mutually immiscible phases are brought into contact wherein one phase is stationary and the other mobile. The sample mixture, introduced into the mobile phase, undergoes a series of interactions i.e. partitions many times between the stationary and mobile phases as it is being carried through the system by the mobile phase. Interactions exploit differences in the physical or chemical properties of the components in the sample. These differences govern the rate of migration of the individual components under the influence of a mobile phase moving through a column containing the stationary phase. Separated components emerge in a certain order, depending on their interaction with the stationary phase. The least retarded component elutes first, the most strongly retained material elutes last. Separation is obtained when one component is retarded sufficiently to prevent overlap with the zone of an adjacent solute as sample components elute from the column.

The chromatographic methods known today can be divided into groups e.g. depending on the nature of the interaction between the stationary phase and the component to be separated. From a physical point of view, the following classification of interactions between molecules is normally used:
  interaction between ions with net charges;
  interaction between permanent dipoles;
  interaction between an ion and a dipole induced by it in another molecule;
  interaction between a permanent dipole and a dipole induced by it in another molecule;
  interaction between non-polar atoms or molecules, such as the inert gases;
  interaction between the nuclei and electrons of one molecule with those of another.

The chromatographic methods suggested up to date are based on one or more of said principles. Thus, for example, in ion-exchange chromatography, the functional groups are permanently bonded ionic groups with their counterions of opposite charge. These counterions can be exchanged for an equivalent number of other ions of the same sign in the mobile phase. Thus, ion-exchange chromatography is limited to the analysis of ionised or ionisable compounds via charge-charge interactions. However, since ion exchange based separations have hitherto mainly been designed to provide high yields of the separated component, the selectivities achieved are usually relatively low. This is a disadvantage especially for applications where a high purity of product is essential, such as in the drug industry.

Alternatively, chromatographic methods can be based on hydrophobic interaction between the stationary phase and the component to be separated, known as hydrophobic interaction chromatography (HIC). Such methods include a hydrophobic stationary phase and a polar mobile phase, which is usually partly or filly aqueous. Polar substances prefer the mobile phase and elute first. As the hydrophobic character of a compound increase, retention becomes longer. Generally, the lower the polarity of the mobile phase, the higher is its eluent strength. Adsorption and desorption are supported by increasing or decreasing, respectively, the salt concentration of the liquid or changing the charge on the ligand and/or the substance to be adsorbed/desorbed by changing pH. HIC methods are e.g. described in WO 9600735, WO 9609116 and U.S. Pat. No. 5,652,348. However, in some instances, the salt required in HIC methods can be undesired, e.g. when the purity of the product is of importance, such as in drug development.

An alternative method that also utilises hydrophobic interaction is based on thiophilic adsorbents, see e.g. Berna et al, Journal of Chromatography A, 800 (1998), 151-159. Thus, here as well, high concentrations of salt can promote different types of molecular interactions, and therefore thiophilic adsorbents will be most useful for purposes similar to the ones of the above-mentioned HIC methods.

Chromatography methods can also be based on affinity between the ligand and compound to be separated. Examples of such useful affinities e.g. are antibody-antigen affinity, metal ion affinity and receptor-ligand affinity. Thus, affinity based methods are very specific procedures, and consequently a ready-made medium cannot be used for more general applications.

The combination of two or more of the known separation principles has been denoted mixed mode ion-exchangers. See for example WO 9729825 (Amersham Pharmacia Biotech AB, Uppsala, Sweden), wherein mixed mode anion-exchangers are described. In some context, this kind of ion-exchangers is denoted multi-mode ion-exchangers. However, the main interaction utilised in these methods has hitherto been ionic.

Recently, a type of ligands denoted high salt ligands (HSL) has been disclosed, see e.g. WO 0011605 (Amersham Pharmacia Biotech AB, Uppsala, Sweden). These ligands, which all carry a charge, can function as mixed mode cation-exchange ligands, and have been shown to be of interest in industrial applications such as protein purification, since they can withstand high salt concentrations and accordingly does not require any substantial dilution of the sample. Naturally, these methods are most advantageous in cases where the product is obtained in a liquid where the salt concentration is already high, such as in fermentation broths or cell lysates.

However, there is wide range of applications today where separation methods are required. For example, the need of high purity products is well recognised within the field of biomedicine, when drugs are to an increased extent manufactured by biotechnological methods. Many separation schemes used in practice are based on a combination of two or more of the principles above, where the product from a first step based one principle, such as ion exchange, is passed onto a second step, where it is submitted to separation based on another principle. Thus, each separation principle can be viewed as one tool useful in a toolbox, where there is a constant need of new tools. Accordingly, despite the known principles mentioned above, there is still a need of novel methods to use as supplement, i.e. as further tools in a tool box, which is improved by increased versatility.

SUMMARY OF THE PRESENT INVENTION

Thus, one object of the present invention is to provide a method of separating a compound from a liquid, which method can give a specificity that differs from prior art methods. Thus, an object of the invention is to provide such a method, which can serve as a supplement or an alternative to known methods of separation.

Another object of the invention is to provide a separation matrix, which enables to achieve such different properties as mentioned above.

A further object of the present invention is to provide a highly efficient elution of a compound, such as a biomolecule, from a separation matrix according to the invention.

One or more of the present objects can be achieved as described in the appended claims. Further embodiments and advantages of the present invention will appear from the detailed description that follows.

Definitions

The term "uncharged" is used herein for a non-ionic compound. An "aromatic group" means herein a conjugated hydrocarbon group with a number of π electrons that equals (4n+2), wherein n is a positive integer or zero (Huckel's rule). The rule applies to hydrocarbons compounds composed of only $sp^2$-hybridized carbon atoms. Groups according to the above wherein a CH=CH unit has been replaced by a nitrogen or a sulphur are also included in the term "aromatic groups".

A group that possesses a "quadrupole" moment is understood to mean a "double dipole". Put differently, a group with a quadrupole moment will have no dipole moment because two dipoles present therein cancel each other out. The term "cation-π interaction" is in some contexts referred to as "π-cation interaction" and means the interaction that appears between the electron dense region formed adjacent to a double bond, such as a conjugated double bond, and a positively charged ion, i.e. a cation. In general, this type of interaction involves compounds that have a local high density of electrons from populated π-orbitals. It has recently been shown that, for simple prototypical aromatic systems, the cation-π interaction is most strongly influenced by an electrostatic term, involving the interaction of the cation with the large, permanent quadrupole moment of the aromatic ring. Even though the study of cation-π interaction has been focused mainly on binding of cations to aromatic systems, cation-π interaction is not restricted to them—it is not a "cation-π aromatic" interaction. Ethylene, acetylene and other simple systems are fully anticipated to and are documented to be involved in cation-interactions (see e.g. Ma, J. C., et al., Chem. Rev. 97 (1997) 1303-1324).

The term "biomolecule" is an abbreviation of a biological molecule and includes organic molecules and compounds, such as proteins and polypeptides, nucleic acids, such as DNA or RNA, plasmids, viruses, cells, organelles, such as nuclei, micro-organisms etc. A "biomolecule" can also be recombinantly manipulated organic molecule or compound, such as a fusion protein.

DETAILED DESCRIPTION OF THE INVENTION

Figure 1:
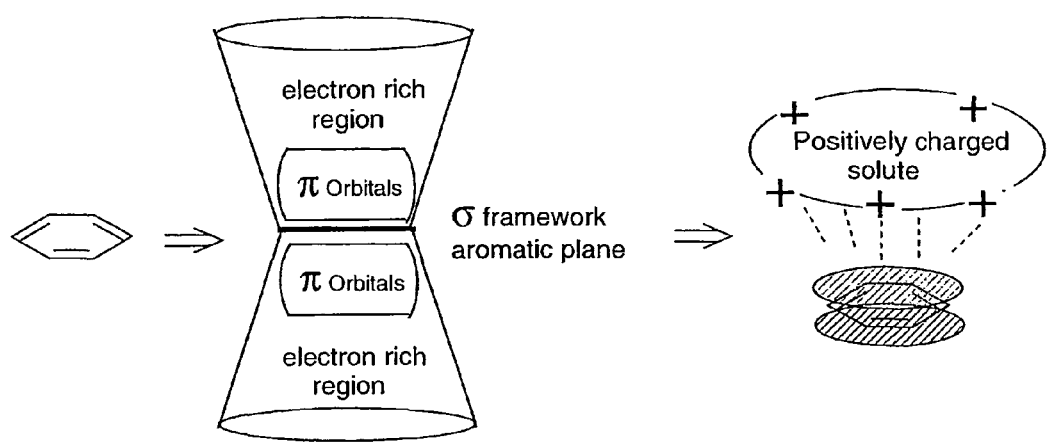
FIG. 1 illustrates the potential interactions between a positively charged solute and a compound with a localised high density of electrons.

A first aspect of the present invention is a method of separating a compound from a liquid, which method comprises the steps of
(a) Providing a separation matrix comprising at least one uncharged ligand;
(b) Providing a liquid wherein the compound to be separated is present in a positively charged state;
(c) Contacting said matrix with said liquid during a sufficient period of time for adsorption of the compound to the matrix to occur; and
(d) Removing the liquid from the matrix; wherein said uncharged ligand possesses a quadrupole or dipole moment and the adsorption of the compound to said ligand is predominated by cation-π interaction.

In one embodiment, the compound to be separated is an organic molecule, such as a biomolecule, which can be a cation under the appropriate pH conditions. Thus, the compound can be a positively charged protein or peptide. In a specific embodiment, said protein or peptide comprises one or more of the basic amino acids, i.e. arginine (Arg), lysine (Lys), glutamine (Gln) and/or histidine (His). In another embodiment, the compound is a protein or peptide that comprises relatively few or no aromatic amino acids. The compound can alternatively be a plasmid, a cell, such as an animal or plant cell, a cell organelle, a microorganism, a virus etc.

In an advantageous embodiment, the purpose of the present method is to provide a biomolecule of a high purity, especially a biomolecule intended for use within the medical field, where requirements on purity can be extremely high. For optimal results, the novel method according to the invention is advantageously combined with a conventional chromatographic process. In an alternative embodiment, the desired product is the liquid, from which one specific undesired component has been removed, e.g. a toxic compound or the like. Thus, in another embodiment, the compound to be separated is an inorganic substance, such as potassium, sodium etc.

In step (b), the pH of the liquid may need to be adjusted to a value where the compound to be separated is positively charged. Said liquid can be any suitable liquid wherein the compound to be separated can exist as a cation, e.g. an aqueous solution, a buffer, a broth originating from a fermentation process, etc. Thus, the compound to be separated is provided in the liquid as a cation. In some cases, it may be advantageous to increase the net charge of the compound by introducing more positive charges. Accordingly, in one embodiment, the compound to be separated has been modified to include one or more additional positive charges, e.g. by introduction of one or more positively charged protein tags such as histidine (His) tags. His tags are well known to the skilled in this field and such a modification can be performed according to conventional procedures. Consequently, the present method is also useful for the separation of a compound, which is not originally cationic, in which case the method above is preceded by a step wherein such a positive tag is introduced.

Accordingly, the present invention utilises for the first time in separation the kind of non-covalent binding forces that nature itself utilises to assemble the molecules of life, namely the binding of a positively charged compound to an uncharged ligand, known as cation-π interaction. The interaction site of e.g. an aromatic group will essentially be over its centre, where the electric potential is most negative. This binding principle, which is novel in the context of separation, has unexpectedly been shown to be sufficiently strong to allow for an efficient chromatographic separation, as illustrated in the experimental part below. Even though the present inventors do not wish to be bound to a specific theory, it is assumed that a substantial part of the binding energy obtained e.g. by a phenyl group is electrostatic. Other components of the energy obtained by the cation-π interaction may reflect the polarizability of the uncharged group that possesses a quadrupole or dipole moment, such the interaction of the cation with the induced dipole of an aromatic group. Donor-acceptor forces along with dispersion forces may also be involved. The essential factor for the present invention is that the quadrupole or dipole moment will give rise to an electron rich region, i.e. a region of high electron density, the properties of which have now been shown to be sufficient to bind a cationic compound.

As mentioned above, the adsorption utilised in the present method is predominated by cation-π interaction. In one embodiment, this means that the adsorption is based on cation-π interaction to at least about 20%, e.g. 30% or 50%, and preferably at least about 75%. In a specific embodiment, the adsorption obtained is based on cation-π interaction to at least about 80%, and preferably at least about 90%, such as at least about 95%. However, it is noted that the figures above refer to the interaction ligand-compound to be separated, and therefore does not include any additional interactions obtained by using spacers including functional groups as discussed below.

Thus, even though cation-π interaction has been described in a wide range of contexts, previous studies has been e.g. in the protein field, where focus has been on biospecificity. Recently, Gallivan, J. P. et al., Proc. Natl. Acad. Sci. U.S.A., 96 (1999) 9459-9464 showed that cation-π interactions are not only quite strong in aqueous media but also commonly found in protein. However, the recent studies have focused on molecular interactions, such as in biological pathways. The present invention suggests for the first time to utilise such a cation-π interaction for separation purposes, e.g. in chromatography. Thus, it is shown in the present specification that cationic biomolecules can be separated from a liquid using an uncharged ligand under low conductivity conditions. Put differently, the present invention utilises an uncharged hydrophobic ligand in a hydrophilic fashion. This principle differs from the previously suggested HIC methods, since low ionic strengths used in the present method.

In one embodiment of the present method, the functional group of the uncharged ligand that possesses a quadrupole or dipole moment is a system, such as a conjugated system, comprising an aromatic group, a —C═C double bond or a C≡N triple bond. Thus, the ligand may be selected from the group that consists of phenyl, cyclopentadiene, furane, thiophene, toluene, anisole, styrene, acetophenone, naphtalene and antracene, or any derivative thereof that still exhibits the electron density necessary for the purpose of binding a cation. Alternatively, the ligand may comprise nitrogen-containing molecules, such as pyridine or pyrrole, but such ligands may be less preferred in acidic pH ranges since the nitrogen will then exhibit a positive charge that can interfere with the binding of the cationic compound to be separated. The ligand can also be a combination of one or more such systems, and may be designed in a spatial configuration that favours binding of a cation. In the most advantageous case, such different ligands can be combined in order to provide additive effects thereof. Thus, an advantageous embodiment of the present method utilises phenyl or a functional derivative thereof wherein the quadrupole moment is essentially retained. In the present context, the term "functional" refers to the capability of binding to a positively charged compound via a region of high electron density. In addition, any substituent that has no or only a minor negative impact on the functional group's binding properties to a cation may be present. However, by empirically testing the properties of a functional group as a ligand in cation exchange, certain substituents may be found that improve the original binding properties. As an example, specific substituents may participate in an additional hydrogen bond to specific biomolecules. Such modified ligands are naturally included within the term derivative above and are covered by the present invention, since such routine testing will require no further inventive skills once the general principle of using cation-π interaction in chromatography is known. Accordingly, the ligand used in the present method can be a larger molecule that comprises a functional group as defined above and the use of substituents with electron withdrawing or electron donor properties can allow design of the method for each specific purpose. Furthermore, one separation matrix may be comprised of more than one uncharged group that possesses a dipole or quadrupole moment, such as a mixture of aromatic and non-aromatic functional groups.

In one embodiment of the present method, the ligand also comprises a spacer separating the functional group from the support. In a specific embodiment, said spacer comprises one or more further functionalities capable of interacting with the compound to be separated, such as by hydrogen bonding, providing a multi-modal chromatographic matrix. Such spacer molecules, sometimes denoted extenders, linkers or arms, have been described in the literature relating to various chromatographic procedures and can accordingly easily be selected by the skilled in this field, see for example Johansson et al in Journal of Chromatography, 403 (1987) 85-98: "Determination of the leakage from . . . ".

The ligand, which as described above will be comprised of a functional group in the form of an uncharged compound optionally coupled to a spacer, is coupled to a support in accordance with well-known technologies. Such supports may be in the form porous or non-porous beads or particles or a monolith or a membrane (continuous matrices). The shape of the beads/particles may be spherical or irregular. The support material can for example be a polysaccharide gel made from dextran (Sephadex®, Amersham Biosciences AB, Uppsala, Sweden), agarose (Sepharose™, Amersham Biosciences AB, Uppsala Sweden), starch, cellulose (Sephacel, Amersham Biosciences AB, Uppsala Sweden), silica, styrene-divinyl benzene (DVB) (SOURCE®, Amersham Biosciences AB, Uppsala, Sweden), polyacrylamide, polyvinylalcohol etc. Alternatively, the matrices are prepared according to standard methods, such as inverse suspension gelation (see e.g. S Hjertén: Biochim Biophys Acta 79(2), 393-398 (1964) or suspension polymerisation (see e.g. "Styrene based polymer supports developed by suspension polymerization" R Arshady: Chimica e L'Industria 70(9), 70-75 (1988)).

In one embodiment, the support is first prepared, and then coated with the present uncharged groups, that possess a dipole or quadrupole moment, according to well known methods. The present kind of ligand can also be used to coat other surfaces, such as a capillary column, a chip, a compact disc (CD) etc, in order render the surface useful in separation procedures wherein cation-π interaction is utilised.

Another novel aspect of the present invention is the use of a divinyl benzene matrix, such as SOURCE® available from Amersham Biosciences AB, Uppsala, Sweden, directly in chromatography. In this aspect, the regions of high electron density formed adjacent to styren groups present on the matrix surface will provide the functional groups of the ligands. Accordingly, the preparation of the ligands used in the present method can be performed as the separation matrix is manufactured. The above mentioned DVB-based matrices have hitherto been used after an appropriate modification of the surface thereof, e.g. by an activation by epichlorohydrine followed by coupling functional groups thereto. Naturally, novel matrices can also be prepared from other starting materials in order to provide a matrix which is directly useful as the stationary phase in chromatography or similar separation processes. Such a novel matrix can exhibit any one or more of the above discussed uncharged group that possesses a dipole or quadrupole moment. Thus, in another embodiment, the separation matrix can be prepared directly e.g. by conventional emulsion techniques.

Step (c), i.e. the adsorption step, can suitably be performed at low ionic strength. The nature of the liquid used, and more specifically the portion of water therein, will be decided depending on the separation support, as will be discussed below. In the present specification, it is to be understood that the term "low ionic strength" corresponds to an ionic strength, which is too low for use in HIC methods. An example of such a low ionic strength is e.g. <0.2 M, such as about 0.1 M. Thus, since the present method can be used under conditions of very low salt strength, and without any addition of salts, the present separation principle differs from HIC. For example, the invention allows a separation that in total provides a more clean or pure end product than the HIC methods, since less salt will be present.

In one embodiment, the method also includes the step (e) Eluting the adsorbed compound. This is conveniently performed by a pH-gradient/step comprising an increasing pH. Thus, the pH of the eluent is gradually changed so that the charge of the compound to be separated changes towards a less positive charge, and subsequently becomes more and more negatively charged. If more than one compounds have adsorbed to the separation matrix, then the different compounds will elute at different charges depending on their respective composition, and the one or more desired compounds are easily separated from the others. In a specific embodiment, the adsorption during step (c) is performed at pH<pI and the desorption of the compound during the elution step (e) is performed at pH>pI. As the skilled in this field knows, pI is a measure of the isoelectric point of a compound and is defined as the pH at which the net charge of said compound is zero.

In an advantageous embodiment, the elution is performed by adding an organic solvent, such as EtOH, DMSO, $CH_3CN$, DMF, isopropanol etc. In this embodiment the pH is adjusted in order to ensure that the compound to be separated is of negative charge.

In the present context, it is to be understood that for each ligand, a pH window can be defined within which the ligand is uncharged. Accordingly, the adsorption process is run under conditions where the functional group of the ligand is uncharged, but for desorption and elution, the conditions can be changed so that the ligand becomes charged and accordingly repels the compound.

A washing step is optionally included before the elution, which washing may utilise any suitable buffer as is well known to the skilled in this field. The steps discussed above for adsorption and desorption and optionally washing are easily performed by the skilled person in this field according to well known techniques and using conventional and commercially available equipment.

Conveniently, the present method is run as a chromatographic process and accordingly steps (b) and (c) are then performed at the same time, i.e. the liquid is added to one end of the chromatographic column to be allowed exit in the other end, as controlled by conventional chromatographic conditions. The liquid can be added at the top of the column or at the bottom thereof, in which case the procedure is run under expanded bed conditions. The liquid can alternatively be brought to pass the separation matrix essentially horizontally, e.g. by use of centrifugation forces. The separation matrix can then be present in a column in the form of a packed bed, an expanded bed, or any other conventionally used form. Various formats of chromatography are known in the art and the skilled in this field can easily select suitable conditions. Alternatively, the present method may be performed as a conventional batch-wise procedure, wherein the liquid is added to a matrix present in a vessel. Adsorption is allowed to take place, optionally with careful stirring, and after a suitable period of time the liquid is removed, e.g. by filtration. Batch-wise procedures have been used for a long time and can be preferred in certain cases, such as where a prolonged adsorption time is expected.

A further aspect of the present invention is a separation matrix for use in the method defined above comprised of a support to which one or more functional groups have been coupled, which functional groups are uncharged groups that possess a quadrupole or dipole moment, which matrix is capable of adsorbing positively charged substances by cation-π interaction. In the preferred embodiment, the uncharged group is a system, such as a conjugated system, comprising an aromatic group, a C═C double bond or a C≡N triple bond. In an advantageous embodiment, the uncharged group is a phenyl group or a derivative thereof, as discussed above, wherein the quadrupole moment is essentially retained. Further details regarding useful uncharged groups having a sufficient electron density for adsorbing cationic compounds are as described above.

In an advantageous embodiment of the present separation matrix, spacer molecules have been introduced to distance the functional groups from the support. Such spacers will for example facilitate for the functional groups to bind a relatively large compound, such as a protein, without disturbing the binding capacity. In an especially advantageous embodiment, the spacer molecules comprise one or more further functional groups capable of interacting with the same compound as the uncharged groups that possesses a dipole or quadrupole moment. Further details regarding useful spacer molecules are as described above.

The density of ligands present in the separation matrix according to the invention can vary, as shown in the experimental part below. Usually, a high density is desired, since it normally results in a high binding capacity. However, this is a variable that the skilled in this field can select depending on the purpose of the method based on experience or simple routine testing. Considerations that matters to this end are e.g. the size of the compound to be separated, the spatial configuration of the ligand used, whether it is a column or a batch-wise process etc.

In one embodiment, the present separation matrix is for use in cation-exchange chromatography, such as for separation of proteins or peptides. Thus, the above-described uncharged groups that possess a dipole or quadrupole moment are capable of binding to cations by the above-discussed cation-π interaction. This principle has never before been suggested for use in separation procedures such as ion exchange, and it was quite unexpected that said interaction was sufficiently strong for this purpose.

As appears from the above, the present separation matrix is for use in a method as defined above. Thus, in an illustrative embodiment, the present invention relates to a chromatographic separation matrix, wherein agarose beads have been provided with uncharged phenyl groups capable of binding cations, such as proteins, by cation-π interaction. Preferably, the phenyl groups have been attached to the agarose via a suitable spacer, such as an alkyl chain to which one or more hydroxy groups have been attached.

DETAILED DESCRIPTION OF THE DRAWINGS

FIG. 1 illustrates the potential interactions between a positively charged solute and a compound with a localised high density of electrons, shown here with an aromatic ligand.

Figure 2:
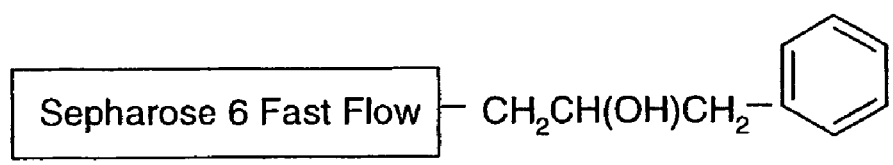
FIG. 2 illustrates the ligand structure of the commercially available Phenyl Sepharose™ Fast Flow matrix (Amersham Biosciences AB, Uppsala, Sweden).

FIG. 2 illustrates the ligand structure of the commercially available Phenyl Sepharose™ Fast Flow matrix (Amersham Biosciences AB, Uppsala, Sweden).

Figure 3:
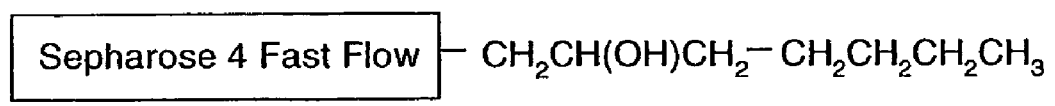
FIG. 3 illustrates the ligand structure of the commercially available Butyl Sepharose™ Fast Flow matrix (Amersham Biosciences AB, Uppsala, Sweden).

FIG. 3 illustrates the ligand structure of the commercially available Butyl Sepharose™ Fast Flow matrix (Amersham Biosciences AB, Uppsala, Sweden).

Figure 4:
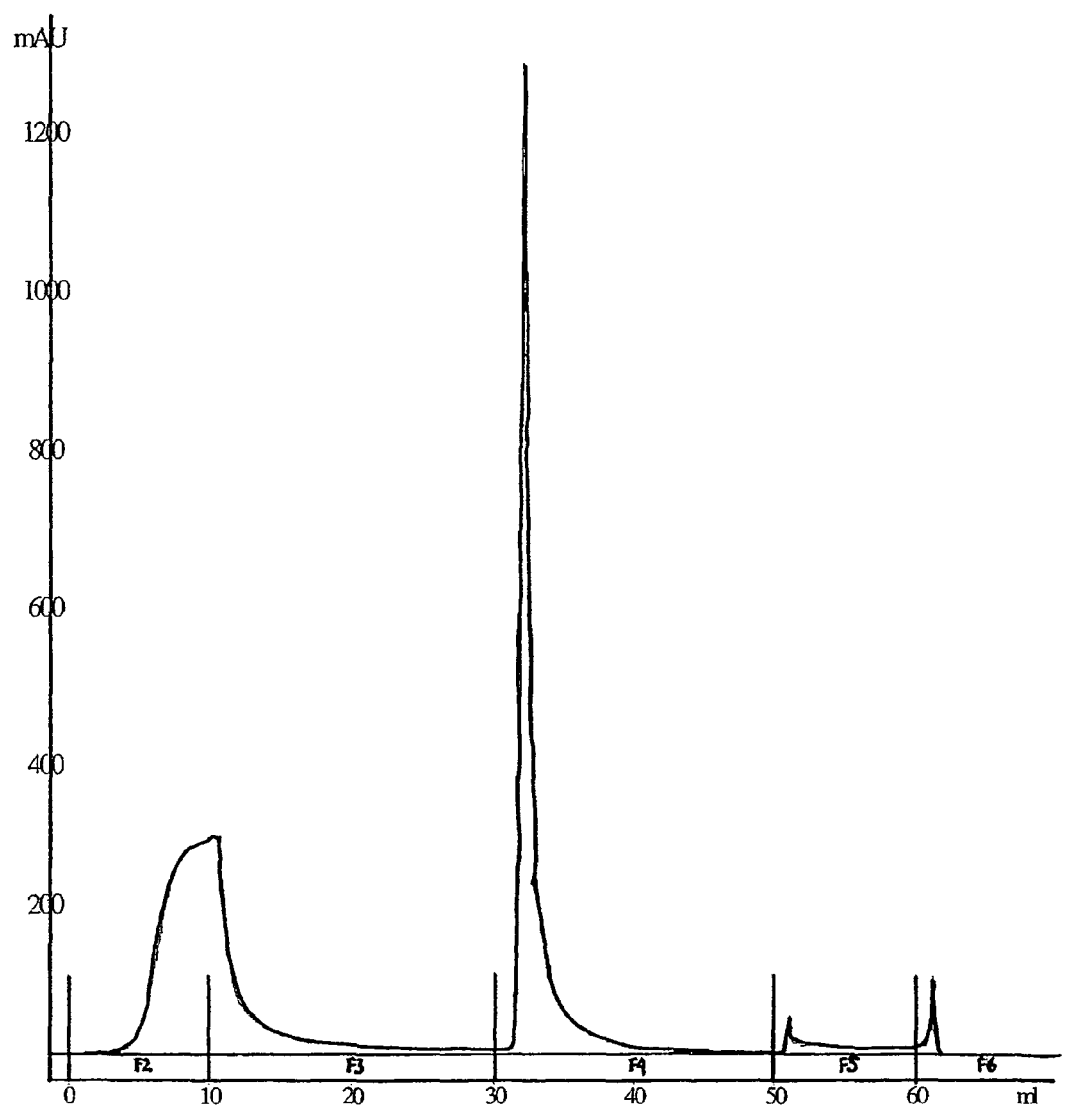
FIG. 4 shows the application of BSA according to Table 1 (experimental part) on a column (HR 5/5 column) packed with Phenyl Sepharose™ Fast Flow

FIG. 4 shows the application of BSA according to Table 1 on a column (HR 5/5 column) packed with Phenyl Sepharose™ Fast Flow (Ligand density =40 μmol/mL gel). This figure shows that by increasing the pH of the mobile phase to pH 7.5, desorption of adsorbed BSA can be obtained. The pI-value of BSA is 5.1. Thus BSA is not attracted to the phenyl ligand as it is negatively charged at pH 7.5.

Figure 5:
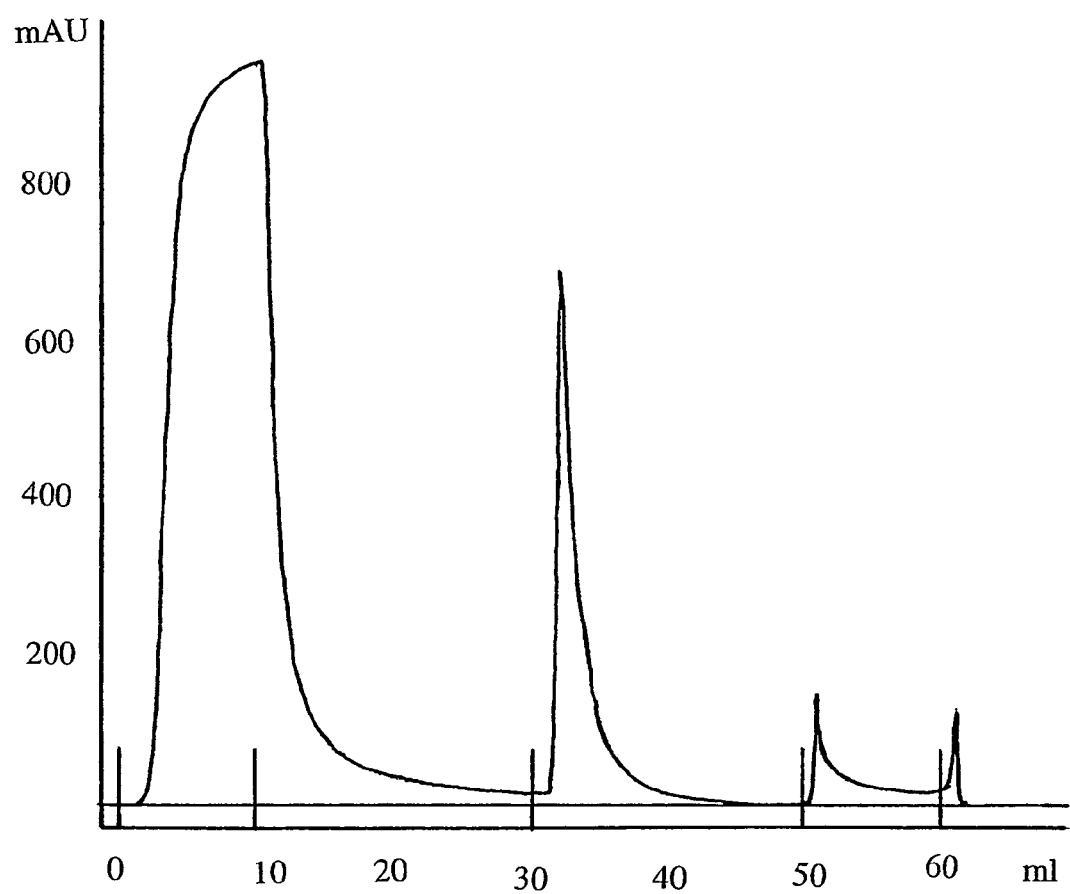
FIG. 5 shows the application of IgG according to Table 1 (experimental part) on a column (HR 5/5 column) packed with Phenyl Sepharose™ Fast Flow.

FIG. 5 shows the application of IgG according to Table 1 on a column (HR 5/5 column) packed with Phenyl Sepharose™ Fast Flow (Ligand density =40 μmol/mL gel). This figure shows that by increasing the pH of the mobile phase to pH 7.5, desorption of adsorbed IgG can be obtained. The pI-value of IgG is about 6. Thus IgG is not attracted to the phenyl ligand as it is negatively charged at pH 7.5.

Figure 6:
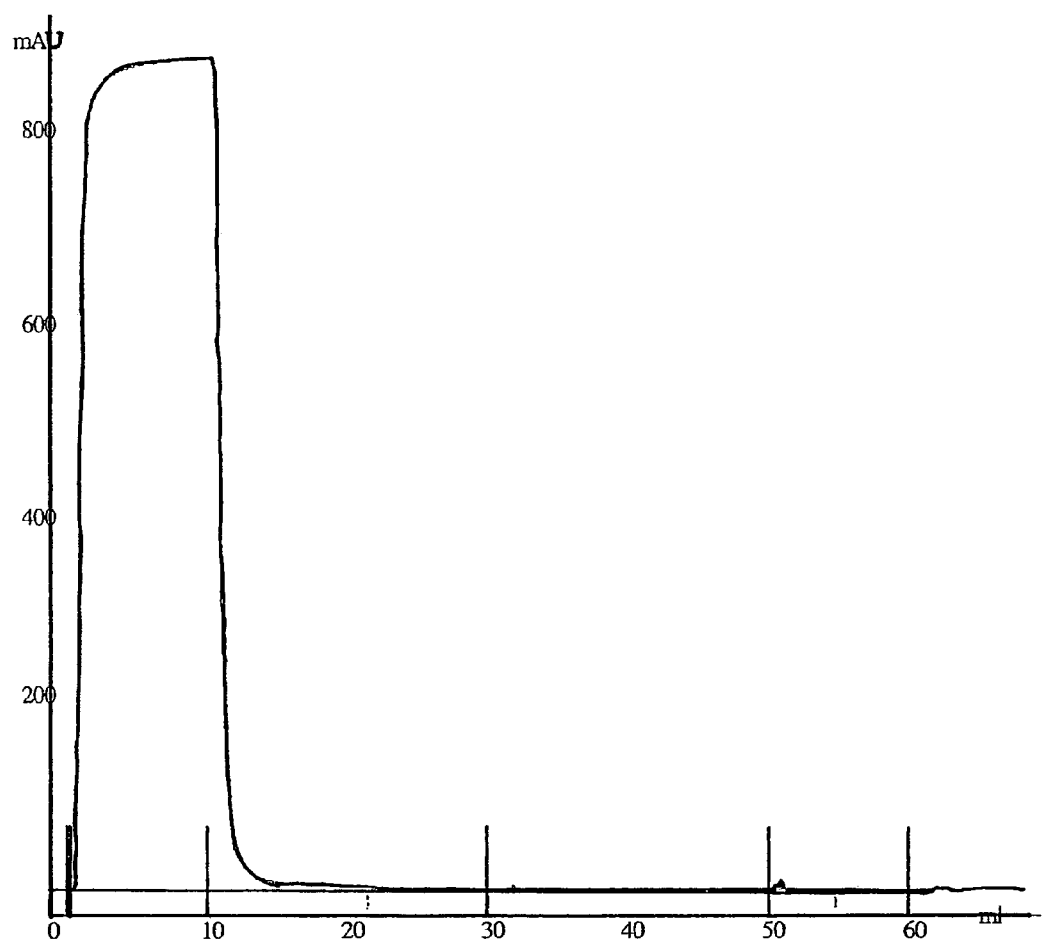
FIG. 6 shows the application of IgG according to Table 1 (experimental part) on a column (HR 5/5 column) packed with Sepharose™ 6 Fast Flow.

FIG. 6 shows the application of IgG according to Table 1 on a column (HR 5/5 column) packed with Sepharose™ 6 Fast Flow, and it appears that IgG is not adsorbed to the base matrix.

Figure 7:
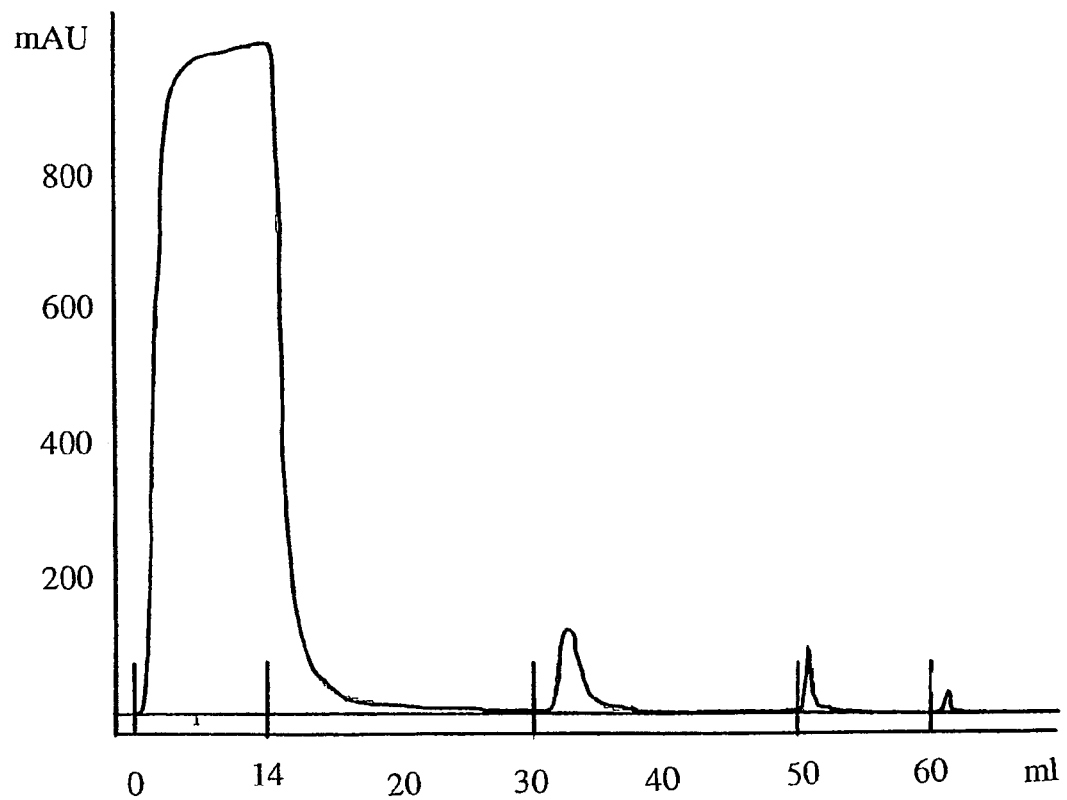
FIG. 7 shows the application of IgG according to Table 1 (experimental part) on a column (HR 5/5 column) packed with Butyl Sepharose™ Fast Flow.

FIG. 7 shows the application of IgG according to Table 1 on a column (HR 5/5 column) packed with Butyl Sepharose™ Fast Flow (Ligand density =50 μmol/mL gel). This figure shows that a small amount of IgG can adsorb to Butyl Sepharose™ Fast Flow and the breakthrough capacity corresponds to 2 mg/mL gel. However, cation-π interactions cannot be the cause for the adsorption of IgG since the butyl ligand does not possess a quadrupole moment.

Experimental Part

Below, the present invention will be illustrated by way of examples. In the experiments presented, phenyl has been used as a representative uncharged group, but it is to be understood that any other uncharged group that possesses a quadrupole or dipole moment can be expected to present similar properties in a separation method according to the invention. Thus, the examples are not to be interpreted as limiting the scope of the present application, which is defined by the appended claims. All references given in the present application are hereby included herein by reference.

Function Test

To verify that cation-π interaction can be used for separation of biomolecules, different positively charged proteins were adsorbed to a separation medium composed of an uncharged ligand (phenyl), attached to the beaded agarose matrix Sepharose™ 6 Fast Flow (FIG. 2). The ligand possesses a quadrupole moment.

Two different ligand densities of Phenyl Sepharose™ Fast Flow were studied, namely 20 μmol/mL gel and 40 μmol/mL gel. See the synthesis procedure section for a brief description of the production of the media.

After adsorption desorption was accomplished at conditions where the test proteins are negatively charged. The separation procedure was as follows. The medium was packed in a column and the protein was applied by pumping a protein solution through the column. The column was then washed to elute non-adsorbed proteins and after the washing step the adsorbed proteins were desorbed. It should be noted that both the adsorption and desorption steps were performed with no extra salt added to the buffer solution used as mobile phase (see below).

The media were packed in 1.0 ml HR 5/5 columns and equilibrated with 20 column volumes of the A-buffer (25 mM acetate buffer; pH 4.0). The protein solutions applied to the columns were 3.2 mg/mL bovine serum albumin (BSA), 4.1 mg/mL human immunoglobuline, 4.9 mg/mL lysozyme, 3.1 mg/mL ribonuclease A, 1.3 mg/ml aldolase, 3.1 mg/mL cytochrome C or 3.8 mg/ml lactoferrin. All proteins were dissolved in the A-buffer. Ten milliliters of these solutions were pumped at a flow rate of 100 cm/h (0.32 mL/min) through the column after equilibration with the A-buffer solution. The breakthrough capacity was evaluated at 10% of the maximum UV detector signal (280 nm). The maximum UV signal was estimated by pumping the test solution directly into the detector. The breakthrough capacity at 10% of maximum absorbance ($Qb_{10}$) was calculated according to the formula:

$$Q_{b10\%} = (T_{R10\%} - T_{RD}) \times C/V_C$$

where $T_{R10\%}$ is the retention time (min) at 10% of maximum absorbance, $T_{RD}$ the void volume time in the system (min), C the concentration of BSA (3.2 mg/mL) and $V_c$ the column volume (mL).

The adsorbed proteins were desorbed using 100 mM phosphate buffer solution (pH 7.5) containing 20% (v/v) ethanol. After desorption the column was cleaned with 1.0 M NaOH to secure that no proteins were left adsorbed to the medium after use. The chromatographic procedure is summarised in Table 1 below.

All experiments were performed at room temperature using ÄKTA™explorer 100 chromatography system (Amersham Biosciences AB, Uppsala, Sweden) equipped with UNICORN™ 3.1 software (Amersham Biosciences AB, Uppsala, Sweden).

Synthesis Procedure of Phenyl Sepharose™ Fast Flow

The two Phenyl Sepharose™ Fast Flow media used are two commercially available media from Amersham Biosciences AB, Uppsala, Sweden. Both media are prepared via a reaction between phenyl glycidyl ether and Sepharose™ 6 Fast Flow.

Results and Discussion

Among the non-covalent interactions that contribute to protein stability, few are both specific and strong when fully exposed in an aqueous medium. There is, however, one relatively underappreciated non-covalent binding force which is potentially both specific and strong in an aqueous environment, namely cation-π interaction. Recent studies have shown that cation-π interactions are not only quite strong in aqueous media but also commonly found in protein structures (Gallivan, J. P. et al., Proc. Natl. Acad. Sci. U.S.A., 96 (1999) 9459-9464). From an electrostatic point of view, the dominating component in cation-π interactions is the attraction of a positively charged molecule toward the quadrupole created by the π-electron cloud of an aromatic ring (Minoux, H. et al., J. Am. Chem. Soc. 121(1999)10366-10372).

FIGS. 4 and 5 illustrate that BSA and IgG can adsorb to Phenyl Sepharose™ Fast Flow at acidic conditions (pH 4.0). To strengthen the electrostatic interaction between the positively charged protein and the uncharged ligand no extra salt was added to the mobile phase except for the buffer components. The breakthrough capacity ($Q_{b10\%}$) of BSA and IgG was determined to be 17 and 9.4 mg/ml, respectively. FIGS. 4 and 5 also show that by increasing the pH of the mobile phase to pH 7.5, desorption of adsorbed BSA and IgG can be obtained. The pI-values of BSA and IgG are 5.1 and about 6, respectively. Thus BSA and IgG are not attracted to the phenyl ligand as they are negatively charged at pH 7.5. Ethanol is added (20% V/V) to the adsorption buffer to slightly sharpen the elution peaks.

The breakthrough capacity of IgG has also been tested for Phenyl Sepharose™ Fast Flow with low ligand density (ligand density 20 μmol/mL). The obtained $Q_{b10\%}$-value of IgG for this medium was 5.5 mg/mL. The $Q_{b10\%}$-value of IgG for high substituted Phenyl Sepharose™ Fast Flow (ligand density 40 μmol/mL) was 9.4 mg/mL indicating that the breakthrough capacity increases with ligand density.

To verify that only the ligand and not the agarose base matrix is interacting with the sample molecules, IgG was applied to a column packed with Sepharose™ 6 Fast Flow (no ligand attached to the beaded agarose matrix). According to FIG. 6 it can be seen that IgG is not adsorbed to the base matrix Sepharose™ 6 Fast Flow.

To verify the importance of cation-π interaction in the case of Phenyl Sepharose™ Fast Flow it was also tested if IgG can adsorb to a medium based on a butyl ligand (FIG. 3). Butyl Sepharose™ Fast Flow is a commercially available medium from Amersham Biosciences AB and has a butyl ligand density corresponding to 50 μmol/mL gel.

FIG. 7 shows that a small amount of IgG can adsorb to Butyl Sepharose™ Fast Flow and the breakthrough capacity corresponds to 2 mg/mL gel. Cation-π interactions cannot be the cause for the adsorption of IgG since the butyl ligand does not possess a quadrupole moment. However, the breakthrough capacity for Butyl Sepharose™ Fast Flow is less than 25% of the capacity observed for Phenyl Sepharose™ Fast Flow (ligand density 40 μmol/mL gel). These results indicate that the force between IgG and the Phenyl ligand is not only due to cation-π interactions. However, cation-π interaction is the most important to obtain high breakthrough capacities.

One advantage with this separation technique would be the selectivity since it is now clear that cation-π interactions are an important binding force that Nature use to assemble the molecules of life (Ma, J. C., et al., Chem. Rev. 97 (1997) 1303-1324). To test this the breakthrough capacity of seven different proteins was measured on Phenyl Sepharose™ Fast Flow. Table 2 below shows that it is a large variation in the $Qb_{10}$-values of the different proteins that clearly indicate that high selectivity can be accomplished with this new separation principle.

TABLE 1

Chromatographic procedure for cation-π interaction

| Step | Explanation | Solution | Flow-rate (mL/min) | Volume (mL) |
|---|---|---|---|---|
| (F2)[a] | Sample application | Protein solution[b] | 0.32 | 10 |
| (F3)[a] | Wash out of sample excess | 25 mM acetate buffer (pH 4.0) | 0.64 | 20 |
| (F4)[a] | Desorption of adsorbed sample molecules | 100 mM phosphate buffer in 20% ethanol (pH 7.5) | 0.64 | 20 |
| (F5)[a] | Cleaning in place | 1.0 M NaOH | 0.64 | 10 |
| (F6)[a] | Re-equilibration before step F2 | 25 mM acetate buffer (pH 4.0) | 0.64 | 10 |

[a]The different steps are depicted in the presented figures.
[b]The protein solutions applied to the column were 3.2 mg/mL bovine serum albumin (BSA), 4.1 mg/mL human immunoglobuline, 4.9 mg/mL lysozyme, 3.1 mg/mL ribonuclease A, 1.3 mg/mL aldolase, 3.1 mg/mL cytochrome C or 3.8 mg/ml lactoferrin dissolved in 25 mM acetate buffer (pH 4.0).

TABLE 2

Breakthrough capacity ($Ob_{10}$) of seven different proteins on Phenyl Sepharose ™ Fast Flow (ligand density 40 μmol/mL gel)

| Protein | Breakthrough capacity (mg/mL) |
|---|---|
| Bovine serum albumin | 17.3 |
| Human IgG | 9.4 |
| Lysozyme | 6.5 |
| Lactoferrin | 5.3 |
| Aldolase | 5.1 |
| Ribonuclease A | 1.8 |
| Cytochrome C | 1.7 |

What is claimed is:

1. A method of separating one or more proteins from an aqueous solution, which method comprises the steps of:
   (a) providing a separation matrix including a C=C double bond or a C≡N triple bond or an aromatic group as at least one uncharged ligand;
   (b) providing an aqueous solution wherein each protein to be separated is present in a positively charged state;
   (c) contacting, under a low ionic strength of less than 0.2 M, said matrix with said aqueous solution for a sufficient period of time to permit adsorption of each protein to the ligand to occur while maintaining each of said protein in a positively charged state;
   (d) removing the aqueous solution from the matrix; and
   (e) eluting at least one protein from the separation matrix; wherein each protein to be separated includes one or more basic amino acids, wherein the adsorption of each protein to said ligand is predominated by cation-π interaction and wherein the adsorption during step (c) is performed at a pH<pI, and the desorption during step (e) is performed at a pH>pI.

2. The method of claim 1, wherein the ligand is coupled to a support via a spacer, which spacer distances the ligand from the support.

3. The method of claim 2, wherein said spacer includes one or more functionalities capable of interacting with the protein to be separated.

4. The method of claim 1, wherein the elution is performed by adding an organic solution.

5. The method of claim 1, wherein said low ionic strength is about 0.1 M.

* * * * *